United States Patent
Li et al.

(10) Patent No.: US 7,141,412 B2
(45) Date of Patent: Nov. 28, 2006

(54) PROCESS FOR PREPARING OPTICALLY ACTIVE 3-HYDROXYPYRROLIDINE DERIVATIVES BY ENZYMATIC HYDROXYLATION

(75) Inventors: Zhi Li, Zurich (CH); Bernard Witholt, Zurich (CH)

(73) Assignee: Eidgenossische Technische Hochschule Zurich, Zurich (CH)

( * ) Notice: Subject to any disclaimer, the term of this patent is extended or adjusted under 35 U.S.C. 154(b) by 430 days.

(21) Appl. No.: 10/372,483

(22) Filed: Feb. 24, 2003

(65) Prior Publication Data

US 2003/0219883 A1    Nov. 27, 2003

Related U.S. Application Data

(63) Continuation of application No. 09/434,906, filed on Nov. 5, 1999, now abandoned.

(30) Foreign Application Priority Data

Nov. 17, 1998  (EP) .................................. 98203893

(51) Int. Cl.
*C12P 17/10*      (2006.01)
(52) U.S. Cl. ...................... 435/280; 435/123; 435/170

(58) Field of Classification Search ...................... None
See application file for complete search history.

(56) References Cited

FOREIGN PATENT DOCUMENTS

GB     1140055      4/1996
JP     WO98/23768   4/1998

OTHER PUBLICATIONS

Parishakov, et al., *Microboial transformations of nitorgen-containing heterocyclic compounds*, XP-002100836, Jan. 4, 1993.

*Primary Examiner*—Irene Marx
(74) *Attorney, Agent, or Firm*—Hoffmann & Baron, LLP

(57) ABSTRACT

A process for the preparation of optically active 3-hydroxypyrrolidine or N-substituted 3-hydroxypyrrolidines, wherein an oxygen atom is inserted stereoselectively into the corresponding pyrrolidines, respectively, by use of a bacterium having hydroxylation activity, or a prokaryotic host-organism having the gene(s) necessary for the hydroxylation, or an enzyme having hydroxylation activity derived therefrom. The bacterium may be selected from strains having alkane hydroxylases, strains degrading alkanes or mono-alicyclic compounds, or strains from the genera *Pseudomonas, Mycobacterium, Corynebacterium, Nocardia, Sphingomonas, Gordona, Rhodococcus, Bacillus, Streptomyces*; *Sebekia* and *Methylococcus*.

27 Claims, No Drawings

PROCESS FOR PREPARING OPTICALLY ACTIVE 3-HYDROXYPYRROLIDINE DERIVATIVES BY ENZYMATIC HYDROXYLATION

This application is a continuation of U.S. application Ser. No. 09/434,906, filed on Nov. 5, 1999, now abandoned; which claims benefit of European Application No. EPO 98203893.7, filed on Nov. 17, 1998. The entire disclosures of the aforementioned applications are incorporated herein by reference.

FIELD OF THE INVENTION

The present invention relates to a process for preparing optically active 3-hydroxypyrrolidine derivatives, wherein an oxygen atom is inserted stereoselectively into corresponding pyrrolidines by use of biocatalysts. Such optically active 3-hydroxypyrrolidine compounds are useful as intermediates for the preparation of several pharmaceutical products and agricultural chemicals.

DESCRIPTION OF THE PRIOR ART

Optically active 3-hydroxypyrrolidine and N-substituted 3-hydroxypyrrolidine are useful intermediates for the synthesis of several pharmaceuticals, agrochemicals, and the like.

In practice it is often advantageous, it not required, to use optically active 3-hydroxypyrrolidine in its N-protected form.

One process for preparing (R)-3-hydroxypyrrolidine involving decarboxylation of (2S,4R)-4-hydroxy-L-proline is known [JP 05/255204 (1993); JP 60/23328 (1985); Hashimoto, M., et al, Chem. Lett., 1986, 893; Mehler, Th., et al, Synthetic Commun. 1993, 23, 2691]. However, the starting material is very expensive.

It is known that (S)-3-hydroxypyrrolidine and its N-substituted derivative can be prepared from L-malic acid by a method including reduction of (S)-N-substituted-3-hydroxy-2,5-pyrrolidinedione with lithium aluminum hydride [Bhat, K. J., et al, Synth. Commun. 1985, 15, 587], sodium borohydride-borotrifluoride-etherate [Chem. Per. 1986, 119, 3327], sodium aluminium hydride [JP 03/200762A2, 1991], sodium bis(2-methoxyethoxy)aluminium hydride [JP 01/254657 A2, 1989], and sodium borohydride [EP 692471 (1996)]. All these reduction reagents are expensive, and difficult to handle; the steps of recovery of the product and destroying of the reagents after reaction are complicated and costly; and some racemization takes place during the reduction.

(S)-3-Hydroxypyrrolidine and its N-substituted derivative can be synthesized from L-glutamic acid [Harris, B. D., et al, Synthetic Commun., 1986, 16, 1815] and L-aspartic acid [shibata, T. et al, Heterocycles, 1986, 24, 1331], respectively. However, these methods are not suitable for large scale production, since six-step syntheses are involved in both methods, including an expensive reduction step.

Optically active 3-hydroxypyrrolidine and its N-substituted derivative can be prepared by reduction of optically active 4-hydroxy-2-pyrrolidinones [JP 01/207266 (1989); JP 01/45360 (1989)], cylization of optically active 4-halo-3-hydroxybutane derivative [EP 452143 (1991)], and cyclization of optically active 4-halo-3-hydroxybutylnitrile derivative [EP 431521 (1991); JP 03/176463 (1991); EP 347818 (1989); EP 269258 (1988)]. Besides other drawbacks, theoptically active starting materials are not easily available and many steps are needed for their preparation.

Processes for preparing optically active 3-hydroxy-pyrrolidine and its N-substituted derivative by classic resolution are known [JP 05/279326 (1993); JP 05/279325 (1993); JP 05/32520 (1993); JP 04/13659 (1992); JP 04/164066 (1992); JP 61163652 (1986)], but the yield is very low.

Processes using enzymatic resolution via hydrolysis [WO 95/03421 (1995); U.S. Pat. No. 5,187,094 (1993); JP 01/141600 (1989); Hasegawa, J., et al, Enantiomer, 1997, 2, 311; Tomori, H., et al, Bull. Chem. Soc. Jpn., 1996, 69, 207] and esterification [WO 95/03421 (1995); JP 05/227991 (1993); JP 04/131093 (1992); Horiguchi, A., et al, Biosci. Biotech. siochem., 1995, 59, 1287] are also known. However, the yield is lower than 50%, the maximum theoretical yield of resolution; the separation of product is difficult. A big drawback for all the resolution processes is the lack of a practical synthesis of the racemic starting materials.

Optically active N-substituted 3-hydroxypyrrolidine can be prepared by hydroboration of N-substituted 3-pyrroline with diisopinocampheylborane followed by oxidation with alkaline hydrogen peroxide [Brown, H. C., et al, J. Am. Chem. Soc., 1986, 108, 2049; Brown, H. C., et al, J. Org. Chem., 1956, 51, 4296]. This method, however, is not suitable for industrial production because of the use of the special borane reagent.

It is known that enzymatic reduction of N-benzyl-3-pyrrolidinone affords optically active N-benzyl-3-hydroxy-pyrrolidine [JP 06/141876 (1994); WO98/23768 (1998)], but the lack of a practical synthesis of the starting material remains one of the drawbacks of this process.

A more direct and economic method for preparing optically active 3-hydroxypyrrolidine and N-substituted derivatives of it, would be the stereoselective insertion of an oxygen into the corresponding pyrrolidines which are easily available. However, this reaction is not possible with classical chemical methods.

Enzymatic hydroxylation of pyrrolidines is difficult. Not much is known about such hydroxylation: there are only some reports on the hydroxylation of N-acylpyrrolidine restricted to the use of some specific fungi.

GB1140055 (1970) relates to the hydroxylation of N-acyl heterocyclic compounds with Sporotrichum sulphurescens ATCC 7159.It is doubtful whether the method is applicable to the hydroxylation of N-acylpyrrolidines. The hydroxylation of N-acylpyrrolidine with Sporotrichum sulphurescens ATCC 7159 is not exemplified in GB1140055. It is known that hydroxylation of N-benzoylpyrrolidine with ATCC 7159 does not give any amount of N-benzoyl-3-hydroxy-pyrrolidine [Srairi, D. et al, Bull. Soc. Chem. Fr. 1987, 297]. It is also known that ATCC 7159 cannot catalyse the hydroxylation of N-aryl- or N-benzyl-pyrrolidine [Floyd, N. et al, J. Chem. Soc. Perkin Trans. 1, 1993, 881]. It is known that hydroxylation of N-benzoylpyrrolidine with Cunninghamella verticillate or Aspergillus niger gives N-benzoyl 3-hydroxypyrrolidine (Chemical Abstracts, 1993, 118: 6835c). However, these processes are not practical, since such hydroxylations with fungi result in low yield, low concentration and low enantiomeric excess (e.e.) of the product, low speed of biotransformation, and formation of byproduct.

SUMMARY OF THE INVENTION

This invention provides a process for the preparation of optically active 3-hydroxypyrrolidine or N-subtituted 3-hydroxypyrrolidines, wherein an oxygen atom is inserted stereoselectively into the corresponding pyrrolidines, respectively, by use of a bacterium having hydroxylation activity, or a prokaryotic host-organism having the gene(s) necessary for the hydroxylation, or an enzyme having hydroxylation activity derived therefrom.

More specifically, the bacterium used is selected from the group consisting of strains having alkane hydroxylases, strains degrading alkanes or mono-alicyclic compounds, or strains from the genera *Pseudomonas, Mycobacterium, Corynebacterium, Nocardia, Sphingomonas, Gordona, Rhodococcus, Bacillus, Streptomyces*, Sebekia, and *Methylococcus*. Preferred are n-alkane-degrading strains, such as the isolates HXN-200 and HXN-1100, *Pseudomonas oleovorans* and *Pseudomonas putida* strains, such as *Pseudomonas oleovorans* GPo1 (ATCC 29347) and *Pseudomonas putida* P1. The invention includes the use of recombinant bacteria having the gene(s) necessary for the hydroxylation, such as one or more of the alkane hydroxylase genes, and especially the multicomponent alkane hydroxylase genes from an alkane degrading bacterium (e.g. from *Pseudomonas oleovorans* GPo1). Preferred are recombinant *Escherichia coli* strains, such as *Escherichia coli* GEc137 (pGEc47).

The biotransformation is performed in vivo with resting cells as biocatalysts, in vivo with growing cells as biocatalysts, or in vitro with crude cell extracts or enzyme preparations that are purified or partially purified as biocatalysts.

The biocatalysts can be immobilized on or in a water-insoluble carrier or support system.

The biotransformation is performed in aqueous medium or in multiphase media possibly containing two or more of the following: a solid phase, an aqueous phase, an organic phase, or a gaseous phase.

The reaction temperature is 5–50° C., preferably at 20–400° C. and the pH of the medium is 4–10, preferably 6–8.

The isolation of optically active 3-hydroxypyrrolidine derivatives may be performed by means of extraction, or by separation techniques such as chromatography using an inorganic, organic, or synthetic adsorbent as a support, or by membrane filtration.

In a preferred embodiment, optically active N-benzyl-3-hydroxypyrrolidine was prepared by stereoselective insertion of an oxygen atom into N-benzylpyrrolidine by use of *Pseudomonas oleovorans* GPo1, or *Pseudomonas putida* P1, or the isolate HXN-200, or the isolate HXN-1100, or other bacteria having alkane hydroxylase or degrading alkanes or mono-alicyclic compounds containing 4 or more C atoms, or a prokaryotic host-organism having the gene(s) necessary for the hydroxylation, such as the recombinant strain *Escherichia coli* GEc137 (pGEc47), or an enzyme derived therefrom.

In a preferred embodiment, optically active N-benzoyl-3-hydroxypyrrolidine, N-benzyloxycarbonyl-3-hydroxypyrrolidine, N-phenoxycarbonyl-3-hydroxypyrrolidine, and N-tert-butoxycarhonyl-3-hydroxypyrrolidine were prepared by stereo-selective insertion of an oxygen atom into N-benzoylpyrrolidine, N-benzyloxycarbonyl-pyrrolidine, N-phenoxycarbonylpyrrolidine, and N-tert-butoxycarbonylpyrrolidine, respectively, by use of the isolate HXN-200, or other bacterium having alkane hydroxylase or degrading alkanes or mono-alicyclic compounds, such as hydrocarbons containing 4 or more C atoms, or a prokaryotic host-organism having the gene(s) necessary for the hydroxylation, or an enzyme having hydroxylation activity derived therefrom.

Optically active N-substituted 3-hydroxypyrrolidine obtained by this process can be easily converted into optically active 3-hydroxypyrrolidine by deprotection.

Thus, the invention described herein provides a useful method for the preparation of optically active 3-hydroxypyrrolidine and N-substituted 3-hydroxypyrrolidine.

DESCRIPTION OF THE INVENTION

Here we have developed a process for the preparation of optically active 3-hydroxypyrrolidine or N-substituted 3-hydroxypyrrolidines, wherein an oxygen atom is inserted stereoselectively into the corresponding pyrrolidines, respectively, by use of a bacterium having hydroxylation activity, or a prokaryotic host-organism having the gene(s) necessary for the hydroxylation, or an enzyme having hydroxylation activity derived therefrom.

For finding appropriate biocatalysts catalyzing this reaction we have screened many microorganisms. In a typical screening procedure, a microorganism was inoculated in a nutrient medium suitable for growth, and the culture was incubated with shaking at 25–35° C. for 1–3 days. The cells were harvested in the late exponential phase of growth and resuspended to 4–6 g/L in 50 mM phosphate buffer (pH=7–8). Substrate was added to a concentation of 0.5–10 mM. The mixture was shaken at 25–35° C. for 0–2 days. The biotransformation was followed by determination of the product formed and the substrate disappeared. Samples were taken from the reaction mixture and analysed directly by high performance liquid chromatography (HPLC) with a reversed phase column, or the samples were extracted with ethyl acetate and the organic phase was analysed by gas chromatography (GC).

We have also established a screening procedure using a microtiter plate: 96 microorganisms were grown in a microtiter plate, which allowed for efficient screening on a microscale.

It has been found that many bacteria are able to catalyse the hydroxylation of pyrrolidines to give the corresponding optically active 3-hydroxypyrrolidines in high yield and high e.e. Examples of these bacteria are bacteria having alkane hydroxylases, bacteria degrading alkanes or mono-alicyclic compounds, and bacteria from the genera. *Pseudomonas, mycobacterium, Corynebacterium, Nocardia, Sphingomonas, Gordona, Rhodococcus, Bacillus, Streptomyces*, Sebekia, and *Methylococcus*.

It has also been found that the biocatalysts can be prokaryotic host-organisms having gene(s) necessary for the hydroxylation. The recombinant strain *Escherichia coli* GEc137 (pGEc47), for example, is a suitable catalyst.

It has been found that hydroxylation of pyrrolidines can be catalysed by an enzyme having hydroxylation activity derived from the said bacteria to give the corresponding optically active 3-hydroxypyrrolidines.

The biotransformation can be performed in vivo with resting cells as biocatalysts, in viva with growing cells as biocatalysts, or in vitro with purified enzymes or crude cell extracts as biocatalysts.

The biocatalysts can be immobilized on or in a water-insoluble carrier or support system.

The biotransformation can be carried out in aqueous medium. It can also be performed in multiphase media possibly containing two or more of the following: a solid phase, an aqueous phase, an organic phase, or a gaseous phase. Organic solvents with high LogP values can be used as organic phase. This includes alkanes with 5 or more C atoms, dialkyl ethers with 4 or more C atoms, and aromatic hydrocarbons. An example of a suitable organic solvent is hexadecane.

The enzymatic hydroxylations can be carried out, although this is no critical parameter, at a temperature of 5–50° C., preferably at 20–40° C. The pressure can vary within wide limits. In practice the biotransformation is performed at atmospheric pressure. The pH of the reaction medium can be between 4 and 10, preferably between 6 and 8.

The product can be separated by chromatographic techniques with an inorganic, organic, or synthetic adsorbent used as a support. The suitable adsorbents are, for instance, aluminium oxide and silical gel. The product can be isolated also by membrane filtration.

The product can also be separated by means of extraction, wherein the substrate is first recovered from the reaction mixture by extraction with less polar solvent, the remaining reaction mixture is adjusted to pH=10–12, and the product is extracted out with more polar solvent. The extraction agent is preferably selected from the group consisting of alkanes with 5 or more C atoms, dialkyl ethers with 4 or more C atoms, chlorine-containing alkanes with 3 or fewer C atoms, alkyl aromatics with 7–10 C atoms, and carboxylic esters with 3 or more C atoms.

It has been found that optically active N-benzyl-3-hydroxypyrrolidine can be prepared by stereoselective insertion of an oxygen atom into N-benzylpyrrolidine by use of Pseudomonas oleovorans GPo1 (strain ATCC 29347). The bio-transformation can be performed with resting cells, crude cell extracts, and growing cells of Pseudomonas oleovorans GPo1, respectively, demonstrated in example 1–3. The culture of Pseudomonas oleovorans GPo1 can be prepared either by growing in E2 medium with octane as carbon source or by growing in E2 medium with pyruvate as carbon source followed by induction of the alkane oxidation system with dicyclopropylketone (DCPK).

The reaction was followed by analytical HPLC (method A, column: Spherisorb ODS2 (5 µm), 125 mm×4 mm; eluent; acetonitrile/10 mM K-phosphate buffer (pH 7.0) 7:3; flow rate: 1 ml/min; detection wavelength: 210 nm; retention time of N-benzyl-3-hydroxypyrrolidine, 6.5 min; retention time of N-benzylpyrrolidine: 25 min; method B, column: Hypersil BDS-C18 (5 µm), 125 mm×4 mm; eluent: acetonitrile/10 mM K-phosphate buffer (pH 7.0) 1:9; flow rate: 1 ml/min; detection wavelength: 210 nm; retention time of N-benzyl-3-hydroxypyrrolidine: 2.7 min; retention time of N-benzyl-pyrrolidine: 3.7 min).

A procedure for the purification of the product was established. It involved either solvent extraction or chromatography. In the case of solvent extraction, the substrate is first recovered by extraction of the reaction mixture with an apolar solvent, and the product is then extracted with a polar solvent out of the remaining reaction mixture after adjusting the pH to pH=12. Suitable extraction agents are alkanes with 5 or more C atoms, dialkyl ethers with 4 or more C atoms, chlorine-containing alkanes with 3 or fewer C atoms, alkyl aromatics with 7–10 C atoms, and carboxylic esters with 3 or more C atoms. Examples of particularly suitable extraction agents are hexane and ethyl acetate, as apolar and polar solvent, respectively. In the case of chromatography, the reaction mixture was extracted with ethyl acetate, the unreacted substrate was first eluted from a column of aluminium oxide with hexane/ethyl acetate (1:1), and the product was then obtained by washing with methanol.

The pure product was identified as N-benzyl-3-hydroxypyrrolidine by comparing the GC-MS and NMR spectra with the corresponding spectra of authentic compound.

The enantiomeric excess (e.e.) of N-benzyl-3-hydroxypyrrolidine was measured by analytical HPLC with a chiral column [Chiracel OB-H (Daicel), 250 mm×4.6 mm; eluent: hexane/isopropanol (98:2); flow rate: 0.5 ml/min; detection wavelength: 210 nm; retention times: min for the (R)-form and 43.5 min for the (S)-form]. N-benzyl-3-hydroxy-pyrrolidine obtained from the hydroxylation of N-benzylpyrrolidine catalysed by Pseudomonas oleovorans GPo1 has 52% e.e. (R).

In the resting cells experiments with Pseudomonas oleovorans GPo1 (strain ATCC 29347), the yield of N-benzyl-3-hydroxypyrrolidine increases at higher cell concentrations (table 1). It also depends on the concentration of substrate. With a cell concentration of 26.2 g/L, 49% and 62% yield were obtained by hydroxylation of 2 mM and 0.5 mM of N-benzylpyrrolidine, respectively.

As shown in example 2, the reaction is quite fast with crude, cell extracts of Pseudomonas oleovorans GPo1 (strain ATCC 29347). The yield is dependent or the concentration of the crude cell extracts. By use of the crude cell extracts obtained from cell densities of 26.2 g/L, 50% of N-benzyl-3-hydroxypyrrolidine was obtained in 4 h.

In the example 3, 12% of N-benzyl-3-hydroxypyrrolidine was obtained with growing cells of Pseudomonas oleovorans GPo1 (strain ATCC 29347) as biocatalysts.

It has been found that Escherichia coli GEc137 (pGEc47) [described by Eggink, G. et al, in J. Biol. Chem. 1987, 262, 17712; in strain collection of Institute of Biotechnology, ETH Zurich], a recombinant strain carring the genes for a multicomponent alkane hydroxylase from Pseudomonas oleovorans GPo1, catalyses the hydroxylation of N-benzylpyrrolidine. 7%, of (R)-N-benzyl-3-hydroxypyrrolidine with 52% e.e. were obtained by hydroxylation of N-benzylpyrrolidine (0.5 mM) with resting cells (2.5 g/L) of Escherichia coli GEc137 (pGEc47), as shown in example 4.

It has been found that alkane-degrading microorganisms are excellent biocatalysts for the hydroxylation of N-benzylpyrrolidine to optically active N-benzyl-3-hydroxy-pyrrolidine. Examples are bacteria degrading n-alkane containing 4 or more C-atoms. By screening with a microtiter plate, 25 of a set of 70 strains degrading n-hexane, n-octane, n-decane, or n-dodedane, were found to be able to catalyse this hydroxylation (example 5). The enantioselectivity and relative activity of 14 selected alkane-degrading strains are shown in table 3 (example 6). Hydroxylation of N-benzylpyrrolidine with Pseudomonas putida P1 gave (R)-N-benzyl-3-hydroxypyrrolidine in 62% e.e.; hydroxylation of N-benzylpyrrolidine with the isolate HXN-1100 gave (R)-N-benzyl-3-hydroxypyrrolidine in 70% e.e.; surprisingly, hydroxylation of N-benzylpyrrolidine with the isolate HXN-200 gave (S)-N-benzyl-3-hydroxypyrrolidine in 53% e.e. (Pseudomonas putida P1 was isolated with n-octane as carbon source by van Beilen, J., ETH Zurich; the isolates HXN-1100 and HXN-200 were isolated with n-hexane as carbon source by Engesser, K.-H. and Plaggemeier, Th., University of Stuttgart; all these strains are in the strain collection of institute of Biotechnology, ETH Zurich).

Hydroxylation of N-benzylpyrrolidine with resting cells of the isolate HXN-1100 is faster than that with P. oleovorans GPo1. Highest yields of N-benzyl-3-hydroxypyrrolidine were obtained with highest cell concentrations, as shown in table 4 (example 7). Hydroxylation of 0.5, 2, and 5 mM of N-benzylpyrrolidine with 26.3 g/L of cells gave (R)-N-benzyl-3-hydroxypyrrolidine with 70% e.e. in 67%, 49%, and 33% yield, respectively.

Hydroxylation of N-benzylpyrrolidine with resting cells of the isolate HXN-200 gave high-activity. As shown in table 5 (example 8), the average activity in the first 30 min reaches 8.2–9.4 U/g CDW starting with 10–20 mM of N-benzylpyrrolidine. It has been found that addition of 2% glucose in the reaction mixture increases the yield. Table 5 shows the results with 2% glucose and 5.3 g/L of cells: the yield at 5 h is 62%, 48%, 35%, and 27% starting with 5 mM (0.81 g/L), 10 mM (1.61 g/L), 15 mM (2.42 g/L), and 20 mM (3.22 g/L) of N-benzylpyrrolidine, respectively. The product has 53% e.e. of the (s)-enantiomer in all cases.

It has been found that the harvested cells of HXN-200 can be stored at −80° for several months without loss of hydroxylation activity.

It has been found that optically active N-benzoyl-3-hydroxypyrrolidine can be prepared by stereoselective insertion of an oxygen atom into N-benzoylpyrrolidine by use of alkane-degrading strains. Hydroxylation of N-benzoylpyrrolidine in vivo with resting cells of HXN-200 is demonstrated in example 9. The biotransformation was followed by analytical HPLC [column: Hypersil BDS-C18 (5 μm), 125 mm×4 mm; eluent: acetonitrile/10 mM K-phosphate buffer (pH 7.0) 3:7; flow rate: 1 ml/min; detection wavelength: 210 nm; retention time of N-benzoyl-3-hydroxy-pyrrolidine; 1.4 mm; retention time of N-benzoylpyrrolidine: 2.9 min].

A procedure for the purification of the product has been established: the unreacted substrate was removed by extraction of the reaction mixture with hexane; the product was obtained by extraction of the remaining aqueous reaction mixture with ethyl acetate. The product can also be isolated by extraction of the reaction mixture with ethyl acetate followed by chromatography on aluminum oxide. The unreacted substrate was eluted with ethyl acetate first, and then the product was eluted with methanol/ethyl acetate (15/85). The resulting product was identified as N-benzoyl-3-hydroxy-pyrrolidine by comparing the GC-MS spectra and NMR spectra with those of the authentic compound.

It has been found that the hydroxylation of N-benzoylpyrrolidine with resting cells of HXN-200 can be performed at pH between 5.2 and 10.0, preferably between 6–9, shown in table 6.

It has been found that presence of 2–3% glucose in the reaction mixture increases the yield. As shown in table 7, 73% of N-benzoyl-3-hydroxypyrrolidine can be obtained by hydroxylation of N-benzoylpyrrolidine (2 mM) with 3.9 g/L of cells of HXN-200 in the presence of glucose (3%).

It has also been found that optically active N-benzoyl-3-hydroxypyrrolidine can be prepared by hydroxylation of N-benzoylpyrrolidine in viva with growing cells of HXN-200. As shown in example 10, the biotransformation was performed in 2 L scale with growing cells of HXN-200; 88% of conversion and 80% of isolated yield were achieved starting from 1.5 mM of substrate. The e.e. of the product was deduced as >99% e.e. (R) by comparing its optical rotation with that of a synthetic sample of N-benzoyl-3-hydroxypyrrolidine prepared from (R)-3-hydroxypyrrolidine and benzoic anhydride.

It has been found that optically active N-benzyloxycarbonyl-3-hydroxypyrrolidine can be prepared by stereoselective insertion of an oxygen atom into N-benzyloxycarbonyl pyrrolidine by use of alkane-degrading strains. Hydroxylation of N-benzyloxycarbonylpyrrolidine in viva with resting cells of HXN-200 is demonstrated in example 11. N-benzyloxycarbonyl pyrrolidine (2–10 mM) and glucose (0 or 2%) were added to a suspension of 4.3 g/L of the cells in 50 mM K-phosphate buffer (pH=7.5). The mixture was shaken at 30° C. for 5 h. The reaction was followed by analytical HPLC [column: Hypersil BDS-C18 (5 μm), 125 mm×4 mm; eluent: acetonitrile/10 mM K-phosphate buffer (pH 7.0) 35:65; flow rate: 1 ml/min; detection wavelength: 210 nm; retention time of N-benzyloxycarbonyl-3-hydroxypyrrolidine: 2.3 min; retention time of N-benzyloxycarbonyl-pyrrolidine: 8.8 min].

A procedure for the purification of the product has been established: the reaction mixture was adjusted to pH=8–12 followed by extraction with ethyl acetate; the product was separated by chromatography on aluminum oxide: the unreacted substrate was eluted with ethyl acetate/hexane (1:9) first, and the product was then eluted with ethyl acetate. The pure product was identified as N-benzyloxycarbonyl-3-hydroxy-pyrrolidine by comparing the GC-MS spectra and NMR spectra with those of the authentic compound.

As shown in table 8, 100o yield was achieved by hydroxylation of 3.5 mm (0.72 g/L) of N-benzyloxycarbonyl pyrrolidine at a cell density of 4.3 g/L.

The e.e. of N-benzyloxycarbonyl-3-hydroxypyrrolidine has been established by analytical HPLC with a chiral column [Chiralpak AS (Daicel), 250 mm×4.6 mm; eluent: hexane/isopropanol (100.4); flow rate: 1 ml/min; detection wavelengths: 210 nm; retention times: 32.9 min for the (S)-form and 36.7 min for the (R)-form]. N-benzyloxycarbonyl-3-hydroxypyrrolidine obtained has 85% e.e. (R).

Preparation of optically active N-benzyloxycarbonyl-3-hydroxypyrrolidine can also be performed in vivo with growing cells of HXN-200. As shown in example 12, the hydroxylation of N-benzyloxycarbonyl-pyrrolidine (1.23 g, 3 mM) with growing cells of HXN-200 was performed in 2 L scale 100% conversion was reached at 2 h (entry 9 in table 8), and 95% (1.26 g) of pure product was isolated as white powder. The product was identified as N-benzyloxycarbonyl-3-hydroxypyrrolidine by comparing the GC-MS spectra and NMR spectra with those of the authentic compound. The product has 85% e.e (R) determined by chiral HPLC.

It has been found that optically active N-phenoxycarbonyl-3-hydroxypyrrolidine can be prepared by stereo-selective insertion of an oxygen atom into N-phenoxycarbonyl pyrrolidine by use of alkane-degrading strains. Hydroxylation of N-phenoxycarbonyl pyrrolidine in vivo with resting cells of HXN-200 is demonstrated in example 13. The biotransformation was performed with N-phenoxycarbonyl pyrrolidine (2–10 mM), glucose (0 or 2%), and a suspension of 4 6 g/L of the cells in 50 mM K-phosphate buffer (pH=7.5) The reaction was followed by analytical HPLC [column: Hypersil BDS-C18 (5 μm), 125 mm×4 mm; eluent: acetonitrile/10 mM K-phosphate buffer (pH 7.0) 35:65; flow rate: 1 ml/min; detection wavelength: 210 nm; retention time of N-phenoxycarbonyl-3-hydroxypyrrolidine: 1.8 min; retention time of N-phenoxycarbonyl pyrrolidine: 6.0 min]. The product was isolated by chromatography on aluminum oxide: the unreacted substrate was eluted with ethyl acetate/hexane (1:9) first, and then the product was eluted with ethyl acetate. The pure product was identified as N-phenoxycarbonyl-3-hydroxypyrrolidine by comparing the GC-MS spectra and NMR spectra with those of the authentic compound.

As shown in table 9, 100% yield was achieved by hydroxylation of 2 mM of N-phenoxycarbonyl-pyrrolidine at a cell density of 4.6 g/L in the presence of 2% glucose. 80% yield could be reached starting with 5 mM (0.96 g/L) of substrate, 2% of glucose, and 4.6 g/L of cells.

The e.e. of N-phenoxycarbonyl-3-hydroxypyrrolidine was measured by analytical HPLC with a chiral column [Chiralpak AS (Daicel), 250 mm×4.6 mm; eluent: hexane/ isopropanol (100:4); flow rate: 1 ml/min; detection wavelength: 210 nm; retention times: 37.3 min for the (S)-form and 41.1 min for the (R)-form]. The product obtained has 36% e.e, (S).

It has been found that optically active N-tert-butoxycarbonyl-3-hydroxy-pyrrolidine can be prepared by stereoselective insertion of an oxygen atom into N-tert-butoxycarbonyl-pyrrolidine by use of alkane-degrading strains, Hydroxylation of N-tert-butoxycarbonyl-pyrrolidine in vivo with resting cells of HXN-200 is demonstrated in example 14. Hydroxylation of N-tert-butoxycarbonyl-pyrrolidine (5–20 mM) was performed with 5.3 g/L of cells of HXN-200 in 50 mM K-phosphate buffer (pH=7.5) in the presence of glucose (0 or 2%). The reaction was followed by analytical HPLC [column: Hypersil BDS-C18 (5 μm), 125 mm×4 mm; eluent; acetonitrile/10 mM K-phosphate buffer (pH 7.0) 3:7; flow rate: 1 ml/min; detection wavelength: 210 nm; retention time of N-tert-butoxycarbonyl-3-hydroxypyrrolidine: 2.3 min; retention time of N-tert-butoxycarbonyl-pyrrolidine: 11.6 min]. The product was isolated by extraction of the reaction mixture with ethyl acetate followed by chromatography on aluminum oxide with hexane/ethyl acetate (1:1). The pure product was identified as N-tert-butoxycarbonyl-3-hydroxypyrrolidine by comparing the GC-MS spectra and NMR spectra with those of the authentic compound.

As shown in table 10, hydroxylation of 5 mM (0.86 g/L) of substrate with 53 g/L of cells of HXN-200 and 2% of glucose gave 100% yield of N-tert-butoxycarbonyl-3-hydroxy-pyrrolidine; 82% of yield was achieved starting from 10 mM (1.71 g/L) of substrate.

The e.e. of N-tert-butoxycarbonyl-3-hydroxypyrrolidine was determined by analytical HPLC with a chiral column [Chiralpak AS (Daicel), 250 mm×4.6 mm; eluent; hexane/isopropanol (98.2); flow rate: 1 ml/min; detection wavelength; 210 nm; retention times: 16.0 min for the (S)-form and 17.9 min for the (R)-form]. The product obtained has 33% e.e. (R).

It has been found that optically active N-tert-butoxycarbonyl-3-hydroxy-pyrrolidine can be prepared in vivo with growing cells of HXN-200. In example 15, the isolate HXN-200 was inoculated in 2 L of E2 medium with octane vapor as carbon source and grown at 30° C. to a cell density of 4.0 g/L. Glucose (80 ml, 50%) was added, the supply of octane vapor was stopped, and N-tert-butoxycarbonyl pyrrolidine (3.505 g) was added. The reaction was continued for 3 h at pH=7.9–8.0. 100% conversion was reached at 3 h and 95% (3.61 g) of pure product was yielded as white powder.

It has been found that optically active N-benzyl-3-hydroxypyrrolidine, N-benzoyl-3-hydroxypyrrolidine, N-benzyloxycarbonyl-3-hydroxypyrrolidine, and N-tert-butoxycarbonyl-3-hydroxypyrrolidine can be prepared from the corresponding pyrrolidines with cell free extracts of an alkane-degrading strain, respectively. Examples are given with cell free extracts of HX-200. It has also been found that the enzyme catalysing this reaction in HXN-200 is not membrane-bound. As shown in example 16, the cell free extracts were prepared by passage of the cells (12.3 g/L) of HXN-200 in Trig-HCl buffer (pH=8.0) through a French press and removal of the cell debris by centrifugation at 45,000 g for 45 min. Treatment of these crude cell extracts without membrane proteins and NADH (5 mM) with N-benzylpyrrolidine (5 mM), N-benzyloxycarbonylpyrrolidine (5 mM), and N-tert-butoxycarbonyl-pyrrolidine (5 mM), respectively, afforded the corresponding 3-hydroxypyrrolidines in 17%, 7%, and 26% yield, respectively.

It has been found that N-acetyl-3-hydroxypyrrolidine can be prepared by stereoselective insertion of an oxygen atom into N-acetylpyrrolidine by use of strains degrading monoalicyclic compounds containing 4 or more C-atoms. An example is given with a cyclohexane-degrading strain (isolated by Li, Z et al, ETH Zurich; in the strain collection of the Institute of Biotechnology, ETH Zurich). In example 17, 4% of N-acetyl-3-hydroxypyrrolidine was obtained by hydroxylation of 2 mM of N-acetylpyrrolidine with resting cells (5 g/L) of a cyclohexane-degrading strain. The reaction was followed by analytical HPLC [column: Spherisorb ODS2 (5 μm), 125 mm×4 mm; eluent: acetonitrile/10 mM K-phosphate buffer (pH 7.0) 5/95; flow rate: 1 ml/min; detection wavelength: 210 nm; retention time of N-acetyl-3-hydroxypyrrolidine: 2.3 min; retention time of N-acetylpyrrolidine: 7.9 min]. The product was identified by comparing the GC-MS and NMR spectra with the corresponding spectra of the authentic compound.

The specific examples given herein are intended merely as an illustration of the invention and should not be construed as a restriction of the scope of the invention.

EXAMPLES

Example 1

Preparation of Optically Active N-benzyl-3-hydroxypyrrolidine in vivo with Resting Cells of *Pseudomonas oleovorans* GPo1

For entry 1–6 in table 1, *Pseudomonas oleovorans* GPo1 (strain ATCC 29347) was inoculated in E2 medium with octane vapor as carbon source and grown at 30° C. for 10 h, the cells were harvested at a cell density of 1–2 g/L and resuspended to 3–30 g/L in 50 mM K-phosphate buffer (pH 7.0). N-benzylpyrrolidine was added to a final concentration of 0.5–2 mM, and the mixture was shaken at 30° C. for 0–2 days.

For entry 7 in table 1, *Pseudomonas oleovorans* GPo1 (strain ATCC 29347) was inoculated, in E2 medium with 0.4% pyruvate as carbon source at 30° C. for 3 h and then induced with 2 mM DCPK for another 3 h to a cell density of 0.6 g/L. The cells were harvested and resuspended to 3.7 g/L in 50 mM K-phosphate buffer (pH 7.0). N-benzylpyrrolidine was added to a final concentration of 0.5 mM and the mixture was shaken at 30° C. for 0–2 days.

The reaction was followed by analytical HPLC: samples were taken out directly from the reaction mixture at different times, the cells were removed by centrifugation, and the supernatants were analysed by analytical HPLC: method A, column: Spherisorb ODS2 (5 μm), 125 mm×4 mm; eluent: acetonitrile/10 mM K-phosphate buffer (pH 7.0) 7:3; flow rate: 1 ml/min; detection wavelength: 210 nm; retention time of N-benzyl-3-hydroxypyrrolidine: 6.5 min; retention time of N-benzylpyrrolidine: 25.0 min; method B, column: Hypersil BDS-C18 (5 μm), 125 mm×4 mm; eluent: acetonitrile/10 mM K-phosphate buffer (pH 7.0) 1:9; flow rate: 1 ml/min; detection wavelength: 210 nm; retention time of N-benzyl-3-hydroxypyrrolidine: 2.7 min; retention time of N-benzylpyrrolidine: 3.7 min.

The product was isolated according to the following procedure: the reaction mixture was extracted with hexane to remove the unreacted substrate, the remaining aqueous reaction mixture was adjusted to pH=12 by the addition of KOH and extracted with ethyl acetate. The organic phase was dried over MgSO$_4$ and the solvent evaporated. This afforded pure N-benzyl-3-hydroxypyrrolidine.

The product can be also isolated as follows: the reaction mixture was adjusted to pH=12 by the addition of KOH and extracted with ethyl acetate. The organic phase was dried over MgSO$_4$ and the solvent evaporated. The residue was subjected to chromatography on aluminum oxide with a short column. The unreacted substrate was eluted with hexane/ethyl acetate (1:1) first, and then the product was eluted with methanol. The pure product was identified as N-benzyl-3-hydroxypyrrolidine by comparing the GC-MS spectra and NMR spectra with those of the authentic compound. The results are listed in table 1.

TABLE 1

Preparation of (R)-N-benzyl-3-hydroxypyrrolidine by hydroxylation of N-benzylpyrrolidine with resting cells of *Pseudomonas oleovorans* GPo1

| Entry | Substrate (mM) | Cells (g/L) | Yield (%) | | | | |
|---|---|---|---|---|---|---|---|
| | | | 1 h | 3 h | 16 h | 23 h | 43 h |
| 1 | 2 | 5.9 | 3 | 5 | 19 | | |
| 2 | 2 | 13.1 | 8 | 18 | 24 | | 31 |
| 3 | 2 | 26.2 | 15 | 29 | 39 | | 49 |
| 4 | 0.5 | 3.7 | 5 | 15 | | 33 | 31 |
| 5 | 0.5 | 13.6 | 12 | 23 | 30 | | 38 |
| 6 | 0.5 | 26.2 | 19 | 36 | 47 | | 62 |
| 7 | 0.5 | 3.7 | 5 | 13 | | | |

The e.e. of N-benzyl-3-hydroxypyrrolidine was measured by analytical HPLC with a chiral column [Chiracel OB-H (Daicel), 250 mm×4.6 mm; eluent: hexane/isopropanol (98:2); flow rate: 0.5 ml/min; detection wavelength: 210 nm; retention times: 26.1 min for the (R)-form and 43.5 min for the (S)-form]. N-benzyl-3-hydroxypyrrolidine obtained here has 52% e.e. (R).

Example 2

Preparation of Optically Active N-benzyl-3-hydroxypyrrolidine in vitro with Crude Cell Extracts of *Pseudomonas oleovorans* GPo1

*Pseudomonas oleovorans* GPo1 (strain ATCC 29347) was inoculated in E2 medium with octane as carbon source at 30° C. with shaking, for 10 h. The cells were harvested and resuspended in Tris-HCl buffer (pH=7.5) to a concentration of 5–30 g/L. After passage through the French press, the cell debris was removed by centrifugation at 4,000 g, To this crude cell extracts containing membrane proteins was added N-benzylpyrrolidine and NADH to a final concentration of 0.5 mM, respectively. The mixture was shaken at 30° C. for 4 h. Analytical and isolation procedures were as described above. The results are listed in table 2.

TABLE 2

Preparation of (R)-N-benzyl-3-hydroxypyrrolidine by hydroxylation of N-benzylpyrrolidine with cell extracts (CE) of *Pseudomonas oleovorans* GPo1

| Entry | Substrate (mM) | Cells for CE$^1$ (g/L) | NADH (mM) | Yield (%) | | | | | |
|---|---|---|---|---|---|---|---|---|---|
| | | | | 0.5 h | 1 h | 1.5 h | 2 h | 3 h | 4 h |
| 1 | 0.5 | 5.6 | 0.5 | 7 | 10 | 14 | 14 | 13 | 13 |
| 2 | 0.5 | 13.1 | 0.5 | 13 | 21 | 29 | 32 | 40 | 44 |
| 3 | 0.5 | 26.2 | 0.5 | 17 | 30 | 36 | 40 | 46 | 50 |

$^1$CE derived from a cell suspension of the indicated concentration.

Example 3

Preparation of Optically Active N-benzyl-3-hydroxypyrrolidine in vivo with Growing Cells of *Pseudomonas oleovorans* GPo1

*Pseudomonas oleovorans* GPo1 (strain ATCC 29347) was inoculated in E2 medium with octane vapor as carbon source and grown at 30° C. to a cell density of 0.3 g/L. N-benzylpyrrolidine was added to a final concentration of 0.5 mM and the cells were allowed to grow further for 3 days. About 12% of N-benzyl-3-hydroxypyrrolidine were obtained.

Example 4

Preparation of Optically Active N-benzyl-3-hydroxypyrrolidine in vivo with Resting Cells of *Escherichia coli* GEc137 (pGEc47)

*Escherichia coli* GEc137 (pGEc47) (described by Eggink, G. et al, in J. Biol. Chem. 1987, 262, 17712; in the strain collection of the Institute of Biotechnology, ETH Zurich) was inoculated in M9 medium with glucose as carbon source and grown at 37° C. for 10 h to a cell density of 0.2 g/L. Induction was then made by adding DCPK to a concentration of 2 mM. Cells were harvested at a cell density of 0.3 g/L, and resuspended to 2.5 g/L in 50 mM K-phosphate buffer (pH 7.0). N-benzylpyrrolidine (0.5mM) was added and the mixture was shaken at 30° C. for 16 h. Analytical and isolation procedures were as described above. 7% of N-benzyl-3-hydroxypyrrolidine was obtained. The product has 52% e.e. (R).

Example 5

Screening of Alkane-degrading Strains for Hydroxylation of N-benzylpyrrolidine to N-benzyl-3-hydroxy-pyrrolidine Seventy (70) alkane-degrading strains isolated with n-hexane, n-octane, n-decane, or n-dodecane as carbon source (all in the strain collection of Institute of Biotechnology, ETH Zurich) were grown in a deepwell microtiter plate at r.t. in 750 µl of medium that consisted of 20 mM glucose, 20 mM L-aspartate, 100 mM K-phosphate buffer (pH=7.0), and 50% of concentrations of all nutrients of Evans medium with nitrilotriacetic acid as a complexing agent. After 3 days, vapor of a mixture of n-octane, n-decane, and n-dodecane (20:30:50) was supplied as carbon source. The cells were grown for an additional 3 days and harvested by centrifugation. 70 µl of N-benzylpyrrolidine (2 mM) in K-phosphate buffer (50 mM, pH 7.0) were added to the cells, and the mixture was shaken at 30° C. for 24 h. The biotransformation was analysed by HPLC. Twenty-five (25) alkane-degrading strains were found to be able to catalyse the biotransformation of N-benzylpyrrolidine to N-benzyl-3-hydroxy-pyrrolidine. Twelve (12) alkane-degrading strains were selected for further study.

Example 6

Preparation of Optically Active N-benzyl-3-hydroxypyrrolidine in vivo with Resting Cells of Alkane-degrading strains Twelve (12) alkane-degrading strains were inoculated individually in E2 medium with octane vapor as carbon source and grown at 30° C. to a cell density of 1–2 g/L, the cells were harvested and resuspended to 3.6 g/L in 50 mM K-phosphate buffer (pH 7.0). N-Benzylpyrrolidine was added to a concentration of 2 mM and the mixture was shaken at 30° C. for 30 min. Procedures for analysis and isolation were as described above. The e.e. of the resulting N-benzyl-3-hydroxypyrrolidine was determined by analytical HPLC with a chiral column as described above. The results are listed in table 3.

TABLE 3

Enantioselectivity and activity of the hydroxylation of N-benzylpyrrolidine to N-benzyl-3-hydroxypyrrolidine with selected alkane-degrading strains

| Entry | Strains[1] | E.e. of product (%) | Relative activity[2] |
|---|---|---|---|
| 1 | HXN-1100 | 70 (R) | 4 |
| 2 | HXN-400 | 65 (R) | 0.5 |
| 3 | P. putida P1 | 62 (R) | 1 |
| 4 | P. oleovorans GPo1 | 52 (R) | 1 |
| 5 | BC20 | 40 (R) | 1 |
| 6 | HXN-1500 | 25 (R) | 3 |
| 7 | HXN-500 | 10 (R) | 11 |
| 8 | HXN-200 | 53 (S) | 6 |
| 9 | HXN-100 | 10 (S) | 3 |
| 10 | HXN-1900 | <10 (S) | 10 |
| 11 | HXN-1000 | <10 (S) | 1 |
| 12 | HXN-600 | 0 | 3 |

[1]All strains are in the strain collection of Institute of Biotechnology, ETH Zurich; the HXN-series of strains were isolated with n-hexane as carbon source by Engesser, K. -H. and Plaggemeier, Th., University of Stuttgart.
[2]Rates are relative to that obtained with Pseudomonas oleovorans GPo1 over the first 30 min.

Example 7

Preparation of Optically Active N-benzyl-3-hydroxypyrrolidine in vivo with Resting Cells of HXN-1100

The isolate HXN-1100 (isolated with n-hexane as carbon source by Engesser, K.-H. and Plaggemeier, Th., University of Stuttgart; in the strain collection of Institute of Biotechnology, ETH Zurich) was inoculated in E2 medium with octane vapor as carbon source and grown at 30° C. for 10 h, the cells were harvested at a cell density of 1–2 g/L and resuspended to 5–30 g/L in 50 mM K-phosphate buffer (pH 7.0). N-benzylpyrrolidine was added to a final concentration of 0.5–5 mM, and the mixtures were shaken at 30 °C. for 24 h. Procedures for analysis and isolation were as described above. The results are shown in table 4. The e.e. or N-benzyl-3-hydroxypyrrolidine: 70% (R).

TABLE 4

Preparation of (R)-N-benzyl-3-hydroxypyrrolidine by hydroxylation of N-benzylpyrrolidine with resting cells of HXN-1100

| Entry | Substrate (mM) | Cells (g/L) | Yield (%) | | | | | |
|---|---|---|---|---|---|---|---|---|
| | | | 0.5 h | 1 h | 2 h | 3 h | 5 h | 24 h |
| 1 | 0.5 | 5.3 | 5 | 9 | 15 | 19 | 27 | 32 |
| 2 | 0.5 | 13.1 | 9 | 20 | 29 | 38 | 48 | 55 |
| 3 | 0.5 | 26.3 | 14 | 30 | 45 | 56 | 66 | 67 |
| 4 | 2 | 5.3 | 3 | 5 | 8 | 10 | 12 | 16 |
| 5 | 2 | 13.1 | 6 | 12 | 18 | 22 | 27 | 30 |
| 6 | 2 | 26.3 | 10 | 21 | 31 | 38 | 47 | 49 |
| 7 | 5 | 5.3 | 2 | 3 | 4 | 5 | 5 | 7 |
| 8 | 5 | 13.1 | 3 | 7 | 10 | 12 | 16 | 19 |
| 9 | 5 | 26.3 | 7 | 14 | 20 | 23 | 30 | 33 |

Example 8

Preparation of Optically Active N-benzyl-3-hydroxypyrrolidine in vivo with Resting Cells of HXN-200

The isolate HXN-200 (isolated with n-hexane as carbon source by Engesser, K.-H. and Plaggemeier, Th. et al, University of Stuttgart; in the strain collection of Institute of Biotechnology, ETH Zurich) was inoculated in 2 L of E2 medium with octane vapor as carbon source and grown at 30° C., the cells were harvested at a cell density of 2.8 g/L and stored at −80° C. N-benzylpyrrolidine (5–20 mM) and glucose (0 or 2%) was added to a suspension of 5.3 g/L of the cells in 50 mM K-phosphate buffer (pH 7.0), and the mixture was shaken at 30° C. for 5 h. Procedures for analysis and isolation were as described above. The results are listed in table 5, the resulting N-benzyl-3-hydroxypyrrolidine has 53% e.e. (S).

TABLE 5

Preparation of (S)-N-benzyl-3-hydroxypyrrolidine by hydroxylation of N-benzylpyrrolidine with resting cells (5.3 g/L) of HXN-200

| Entry | Substrate (mM) | Glucose (%) | Activity[1] (U/g CDW) | Yield (%) | |
|---|---|---|---|---|---|
| | | | | 0.5 h | 5 h |
| 1 | 5 | | 5.7 | 18 | 38 |
| 2 | 5 | 2 | 6.0 | 19 | 62 |
| 3 | 10 | | 8.2 | 13 | 28 |
| 4 | 10 | 2 | 8.8 | 14 | 48 |
| 5 | 15 | | 8.9 | 11 | 26 |
| 6 | 15 | 2 | 9.4 | 10 | 35 |
| 7 | 20 | | 8.8 | 7 | 17 |
| 8 | 20 | 2 | 7.5 | 6 | 27 |

[1]Activity was determined over a time interval of the first 30 min.

Example 9

Preparation of Optically Active N-benzoyl-3-hydroxypyrrolidine in vivo with Resting Cells of HXN-200

The isolate HXN-200 was inoculated in 2 L of E2 medium with octane vapor as carbon source and grown at 30° C., the cells were harvested at a cell density of 2.8 g/L and stored at −80° C. N-benzoylpyrrolidine (2–5 mM) and glucose (0 or 2%) was added to a suspension of 3–5 g/L of the cells in 50 mM K-phosphate buffer, 50 mM Tris-HCl buffer, and NaHCO$_3$/NaOH buffer at different pH, respectively, The mixture was shaken at 30° C. for 5–24 h.

The reaction was followed by analytical HPLC: samples were taken out directly from the reaction mixture at different times, the cells were removed by centrifugation, and the supernatants were analysed by analytical HPLC [column: Hypersil BDS-C18 (5 μm), 125mm×4 mm; eluent: acetonitrile/10 mM K-phosphate buffer (pH 7.0) 3:7; flow rate: 1 ml/min; detection wavelength: 210 nm; retention time of N-benzoyl-3-hydroxypyrrolidine: 1.4 min; retention time of N-benzoylpyrrolidine: 2.9 min].

The product was isolated according to the following procedure: the reaction mixture was extracted with hexane to remove the unreacted substrate, the remaining aqueous reaction mixture was then extracted with ethyl acetate. The organic phase was dried over $MgSO_4$ and the solvent evaporated. This afforded pure product.

The product can be also isolated as follows: the reaction mixture was adjusted to pH=8–12 by the addition of KOH and extracted with ethyl acetate. The organic phase was dried over $MgSO_4$ and the solvent evaporated. The residue was subjected to chromatography on aluminum oxide with a short column. The unreacted substrate was eluted with ethyl acetate first, and then the product was eluted with methanol/ethyl acetate (15/85). The pure product was identified as N-benzoyl-3-hydroxypyrrolidine by comparing the GC-MS spectra and NMR spectra with those of the authentic compound. The results are listed in table 6–7.

TABLE 6

Preparation of (R)-N-benzoyl-3-hydroxypyrrolidine by hydroxylation of N-benzoylpyrrolidine (2 mM) with resting cells of HXN-200 in different pH

| Entry | pH | Cells (g/L) | Yield (%) 0.5 h | 1 h | 2 h | 3 h | 5 h |
|---|---|---|---|---|---|---|---|
| 1 | 5.2[a] | 3.8 | 3 | 4 | 4 | 4 | 4 |
| 2 | 5.7[a] | 3.8 | 8 | 10 | 10 | 10 | 11 |
| 3 | 6.4[a] | 3.8 | 9 | 11 | 12 | 12 | 13 |
| 4 | 7.0[a] | 3.8 | 9 | 11 | 13 | 13 | 14 |
| 5 | 7.6[a] | 3.8 | 10 | 13 | 14 | 15 | 15 |
| 6 | 7.1[b] | 3.7 | 10 | 11 | 13 | 13 | 13 |
| 7 | 8.1[b] | 3.7 | 11 | 14 | 15 | 15 | 15 |
| 8 | 8.4[b] | 3.7 | 11 | 14 | 15 | 16 | 16 |
| 9 | 8.9[b] | 3.7 | 12 | 16 | 18 | 19 | 20 |
| 10 | 9.1[b] | 3.7 | 11 | 17 | 20 | 22 | 23 |
| 11 | 10.0[c] | 4.4 | 7 | 10 | 16 |  | 22 |
| 12 | 11.0[c] | 4.4 | 0 | 0 | 0 |  | 0 |

[a]50 mM K-phosphate buffer;
[b]50 mM Tris-HCl buffer;
[c]NaHCO3/NaOH buffer

TABLE 7

Preparation of (R)-N-benzoyl-3-hydroxypyrrolidine by hydroxylation of N-benzoylpyrrolidine with resting cells (3.9 g/L) of HXN-200

| Entry | Substrate (mM) | Glucose (%) | Activity[a] (U/g CDW) | Yield (%) 0.5 h | 1 h | 2 h | 3 h | 5 h | 24 h |
|---|---|---|---|---|---|---|---|---|---|
| 1 | 2[b] | 0 | 2.2 | 13 | 17 | 19 | 19 | 20 |  |
| 2 | 2[b] | 2 | 2.2 | 13 | 21 | 33 | 43 | 56 |  |
| 3 | 5[b] | 0 | 2.6 | 6 | 8 | 9 | 9 | 9 |  |
| 4 | 5[b] | 2 | 3.0 | 7 | 10 | 13 | 15 | 19 |  |
| 5 | 2[c] | 2 | 2.2 | 13 | 18 | 26 | 33 | 44 | 70 |
| 6 | 2[c] | 3 | 2.2 | 13 | 18 | 27 | 36 | 48 | 73 |
| 7 | 5[c] | 2 | 3.0 | 7 | 9 | 12 | 13 | 15 | 16 |
| 8 | 5[c] | 3 | 3.0 | 7 | 9 | 12 | 15 | 16 | 19 |
| 9 | 2[d] | 2 | 2.4 | 14 | 22 | 33 | 42 | 53 |  |
| 10 | 2[d] | 3 | 2.4 | 14 | 21 | 32 | 41 | 52 |  |
| 11 | 5[d] | 2 | 3.4 | 8 | 11 | 16 | 19 | 23 |  |
| 12 | 5[d] | 3 | 3.4 | 8 | 11 | 17 | 21 | 27 |  |

[a]Activity was determined over a time interval of the first 30 min;
[b]50 mM K-phosphate buffer (pH = 7.7);
[c]50 mM Tris-HCl buffer (pH = 8.0);
[d]50 mM Tris-HCl buffer (pH = 9.1).

Example 10

Preparation of Optically Active N-benzoyl-3-hydroxypyrrolidine in vivo with Growing Cells of HXN-200

The isolate HXN-200 was inoculated in 2 L of E2 medium in a 3 L bioreactor with octane vapor as carbon source and grown at 30° C. to a cell density of 3.0 g/L. Glucose (80 ml, 50%) was added, the supply of octane vapor was stopped, and N-benzoylpyrrolidine (570 mg) was added. The reaction was continued for 9 h, and pH was kept between 7.2–7.4 during this period. HPLC analysis showed that 88% conversion was reached at 9 h. The cells were removed by centrifugation, and the supernatants were extracted with ethyl acetate after pH was adjusted to 9.0. The organic phase was dried over $MgSO_4$ and the solvent evaporated. The residue was subjected to chromatography on aluminum oxide with a short column. The unreacted substrate was eluted with ethyl actate first, and then the product was eluted with methanol/ethyl acetate (15/85). Yield: 80% (498 mg) of pure product as white powder. White crystals were obtained by crystallization from ethyl acetate. The product was identified as N-benzoyl-3-hydroxypyrrolidine by comparing the GC-MS spectra and NMR spectra with those of the authentic compound. $[\alpha]_D^{25}$ of the product is −94.1 (c=1.047, $CHCl_3$), which indicates >99% e.e of (R)-enantiomer, as a synthetic sample of N-benzoyl-3-hydroxypyrrolidine prepared from (R)-3-hydroxypyrrolidine and benzoic anhydride has $[\alpha]_D^{25}$ of −94.1 (c=1.02, $CHCl_3$).

Example 11

Preparation of Optically Active N-benzyloxy-carbonyl-3-hydroxypyrrolidine in vivo with Resting Cells of HXN-200

The isolate HXN-200 was inoculated in 2 L of E2 medium with octane vapor as carbon source and grown at 30° C., the cells were harvested at a cell density of 2.8 g/L and stored at −80° C. N-benxyloxycarbonyl-pyrrolidine (2–10 mM) and glucose (0 or 2%) was added to a suspension of 4.3 g/L of the cells in 50 mM K-phosphate buffer (pH=7.5). The mixture was shaken at 30° C. for 5 h.

The reaction was followed by analytical HPLC: samples were taken out directly from the reaction mixture at different times, the cells were removed by centrifugation, and the supernatants were analysed by analytical HPLC [column: Hypersil BDS-C18 (5 μm), 125 mm×4 mm; eluent: acetonitrile/10 mM K-phosphate buffer (pH 7.0) 35:65; flow rate:

1 ml/min; detection wavelength: 210 nm; retention time of N-benzyloxycarbonyl-3-hydroxypyrrolidine: 2.3 min; retention time of N-benzyloxycarbonyl-pyrrolidine: 8.8 min].

The product can be isolated as follows; the reaction mixture was adjusted to pH=8–12 by the addition of KOH and extracted with ethyl acetate. The organic phase was dried over MgSO$_4$ and the solvent evaporated. The residue was subjected to chromatography on aluminum oxide with a short column. The unreacted substrate was eluted with ethyl acetate/hexane (1:9) first, and then the product was eluted with ethyl acetate. The pure product was identified as N-benzyloxycarbonyl-3-hydroxypyrrolidine by comparing the GC-MS spectra and NMR spectra with those of the authentic compound. The results are listed in entry 1–8 in table 8.

The e.e. of N-benzyloxycarbonyl-3-hydroxypyrrolidine was measured by analytical HPLC with a chiral column [Chiralpak AS (Daicel), 250 mm×4.6 mm; eluent: hexane/isopropanol (100:4); flow rate: 1 ml/min; detection wavelength: 210 nm; retention times: 32.9 min for the (S)-form and 36.7 min for the (R)-form]. (R)-N-benzyloxycarbonyl-3-hydroxypyrrolidine was obtained in as 85% e.e.

TABLE 8

Preparation of (R)-N-benzyloxycarbonyl-3-hydroxy-pyrrolidine by hydroxylation of N-benzyloxycarbonyl-pyrrolidine with resting cells (4.3 g/L) of HXN-200

| Entry | Substrate[a] (mM) | Glucose (%) | Activity[b] (U/g CDW) | Yield (%) 0.5 h | 1 h | 2 h | 3 h | 5 h |
|---|---|---|---|---|---|---|---|---|
| 1 | 2 | 0 | 4.2 | 27 | 52 | 73 | 88 | 88 |
| 2 | 2 | 2 | 13.1 | 85 | 100 | | | |
| 3 | 3.5 | 0 | 8.7 | 32 | 68 | 93 | 100 | |
| 4 | 3.5 | 2 | 10.3 | 38 | 67 | 96 | 100 | |
| 5 | 5 | 0 | 7.4 | 19 | 44 | 57 | 61 | 57 |
| 6 | 5 | 2 | 8.9 | 23 | 42 | 56 | 56 | 53 |
| 7 | 10 | 0 | 7.8 | 10 | 14 | 14 | 16 | 14 |
| 8 | 10 | 2 | 10.9 | 14 | 19 | 24 | 23 | 20 |
| 9 | 3 | 2 | 15.8 | 68 | 92 | 100 | | |

[a] in 50 mM K-phosphate buffer (pH = 7.5);
[b] activity was determined over a time interval of the first 30 min.

Example 12

Preparation of Optically active N-benzyloxy-carbonyl-3-hydroxypyrrolidine in vivo with Growing Cells of HXN-200

The isolate HXN-200 was inoculated in 2 L of E2 medium in a 3 L bioreactor with octane vapor as carbon source and grown at 30° C. to a cell density of 4.0 g/L. Glucose (80 ml, 50%) was added, the supply of octane vapor was stopped, and N-benzyloxycarbonyl-pyrrolidine (1.23 g) was added. The reaction was continued for 2 h, and pH was kept between 7.9–8.0 during this period. HPLC analysis showed that 100% conversion was reached at 2 h (entry 9 in table 8). The cells were removed by centrifugation, and the supernatants were extracted with ethylacetate after pH was adjusted to 9.0. The organic phase was dried over MgSO$_4$ and the solvent evaporated. This afforded 95% (1.26 g) of pure product as white powder. The product was identified as N-benzyloxy-carbonyl-3-hydroxypyrrolidine by comparing the GC-MS spectra and NMR spectra with those of the authentic compound. The product has 85% e.e. (R) determined by analytical HPLC with a chiral column as described above.

Example 13

Preparation of Optically Active N-phenoxycarbonyl-3-hydroxypyrrolidine in vivo with Resting Cells of HXN-200

The isolate HXN-200 was inoculated in 2 L of E2 medium with octane vapor as carbon source and grown at 300° C., the cells were harvested at a cell density of 2.8 g/L and stored at −80° C. N-phenoxycarbonyl pyrrolidine (2–10 mM) and glucose (0 or 2%) was added to a suspension of 4.6 g/L of the cells in 50 mM K-phosphate buffer (pH=7.5). The mixture was shaken at 30° C. for 5 h.

The reaction was followed by analytical HPLC: samples were taken out directly from the reaction mixture at different times, the cells were removed by centrifugation, and the supernatants were analysed by analytical HPLC [column: Hypersil BDS-C18 (5 μm), 125 mm×4 mm; eluent: acetonitrile/10 mM K-phosphate buffer (pH 7.0) 35:65; flow rate: 1 ml/min; detection wavelength: 210 nm; retention time of N-phenoxycarbonyl-3-hydroxypyrrolidine: 1.8 min; retention time of N-phenoxycarbonyl pyrrolidine: 6.0 min].

The product was isolated as follows: the reaction mixture was adjusted to pH =8–12 by the addition of KOH and extracted with ethyl acetate. The organic phase was dried over MgSO$_4$ and the solvent evaporated. The residue was subjected to chromatography on aluminum oxide with a short column. The unreacted, substrate was eluted with ethyl acetate/hexane (1:9) first, and then the product was eluted with ethyl acetate. The pure product was identified as N-phenoxycarbonyl-3-hydroxypyrrolidine by comparing the GC-MS spectra and NMR spectra with those of the authentic compound. The results are listed in table 9.

The e.e. of N-phenoxycarbonyl-3-hydroxypyrrolidine was measured by analytical HPLC with a chiral column [Chiralpak AS (Daicel), 250 mm×4.6 mm; eluent: hexane/isopropanol (100:4); flow rate: 1 ml/min; detection wavelength: 210 nm; retention times: 37.3 min for the (S)-form and 41.1 min for the (R)-form]. The product obtained has 36% e.e. (S).

TABLE 9

Preparation of (S)-N-phenoxycarbonyl-3-hydroxypyrrolidine by hydroxylation of N-phenoxycarbonyl-pyrrolidine with resting cells (4.6 g/L) of HXN-200

| Entry | Substrate (mM) | Glucose (%) | Activity[1] (U/g CDW) | Yield (%) 0.5 h | 1 h | 2 h | 3 h | 5 h |
|---|---|---|---|---|---|---|---|---|
| 1 | 2 | 0 | 7.1 | 49 | 75 | 92 | 94 | 94 |
| 2 | 2 | 2 | 11.2 | 77 | 100 | | | |
| 3 | 5 | 0 | 3.7 | 10 | 20 | 32 | 36 | 40 |
| 4 | 5 | 2 | 13.3 | 36 | 62 | 72 | 73 | 80 |
| 5 | 10 | 0 | 4.5 | 6 | 16 | 31 | 35 | 37 |
| 6 | 10 | 2 | 11.6 | 16 | 29 | 38 | 38 | 39 |

[1] Activity was determined over a time interval of the first 30 min.

Example 14

Preparation of Optically Active N-tert-butoxycarbonyl-3-hydroxy-pyrrolidine in vivo with Resting Cells of HXN-200

The isolate HXN-200 was inoculated in 2 L of 22 medium with octane vapor as carbon source and grown at 30° C., the cells were harvested at a cell density of 28 g/L and stored at −80° C. N-tert-butoxycarbonyl-pyrrolidine (5–20 mM) and glucose (0 or 2%) was added to a suspension of 5.3 g/L of the cells in 50 mm K-phosphate buffer (pH=7.5). The mixture was shaken at 30° C. for 5 h.

The reaction was followed by analytical HPLC: samples were taken out directly from the reaction mixture at different times, the cells were removed by centrifugation, and the supernatants were analysed by analytical RPLC [column: Hypersil BDS-C18 (5 μm), 125 mm×4 mm; eluent: acetonitrile/10 mM K-phosphate buffer (pH 7.0) 3:7; flow rate: 1 ml/min; detection wavelength: 210 nm; retention time of N-tert-butoxycarbonyl-3-hydroxypyrrolidine: 2.3 min; retention time of N-tert-butoxycarbonyl-pyrrolidine. 11.6 min].

The product was isolated as follows: the reaction mixture was adjusted to pH=8–12 by the addition of KOH and extracted with ethyl acetate. The organic phase was dried over MgSO₄ and the solvent evaporated. The residue was subjected to chromatography on aluminum oxide with a short column with hexane/ethyl actate (1:1). The pure product was identified as N-tert-butoxycarbonyl-3-hydroxypyrrolidine by comparing the GC-MS spectra and NMR spectra with those of the authentic compound. The results are listed in table 10.

The e.e. of N-tert-butoxycarbonyl-3-hydroxypyrrolidine was measured by analytical HPLC with a chiral column [Chiralpak AS (Daicel), 250 mm×4.6 mm; eluent: hexane/isopropanol (92:2); flow rate: 1 ml/min; detection wavelength: 210 nm; retention times: 16.0 min for the (S)-form and 17.9 min for the (R)-form]. The product obtained has 33% e.e. (R).

TABLE 10

Preparation of (R)-N-tert-butoxycarbonyl-3-hydroxy-pyrrolidine by hydroxylation of N-tert-butoxycarbonyl-pyrrolidine with resting cells (5.3 g/L) of HXN-200

| Entry | Substrate (mM) | Glucose (%) | Activity[1] (U/g CDW) | Yield (%) 0.5 h | 1 h | 2 h | 3 h | 5 h |
|---|---|---|---|---|---|---|---|---|
| 1 | 5 |   | 18.6 | 59 | 77 | 87 | 87 | 90 |
| 2 | 5 | 2 | 21.4 | 68 | 92 | 100 |   |   |
| 3 | 10 |   | 23.9 | 38 | 61 | 69 | 73 | 77 |
| 4 | 10 | 2 | 21.4 | 34 | 61 | 68 | 74 | 82 |
| 5 | 15 |   | 17.9 | 19 | 34 | 36 | 36 | 44 |
| 6 | 20 |   | 11.3 | 9 | 13 | 15 | 16 | 20 |

[1]Activity was determined over a time interval of the first 30 min.

Example 15

Preparation of Optically Active N-tert-butoxy-carbonyl-3-hydroxy-pyrrolidine in vivo with Growing Cells of HXN-200

The isolate HXN-200 was inoculated in 2 L of P2 medium in a 3 L bioreactor with octane vapor as carbon source and grown at 30° C. to a cell density of 4.0 g/L. Glucose (80 ml, 50%) was added, the supply of octane vapor was stopped, and N-tert-butoxycarbonyl-pyrrolidine (3.505 g) was added. The reaction was continued for 3 h, and pH was kept between 7.9–8.0 during this period. HPLC analysis showed that 100% conversion was reached at 3 h. The cells were removed by centrifugation, and the supernatants were extracted with ethylacetate after pH was adjusted to 9.0. The organic phase was dried over MgSO₄ and the solvent evaporated. This afforded 95% (3.61 g) of pure product as white powder.

Example 16

Preparation of Optically Active N-benzyl-3-hydroxypyrrolidine, N-benzyloxycarbonyl-3-hydroxypyrrolidine, and N-tert-butoxycarbonyl-3-hydroxypyrrolidine in vitro with Crude Cell Extracts of HXN-200

The isolate HXN-200 was inoculated in 2 L of E2 medium in a 3 L bioreactor with octane vapor as carbon source and grown at 30° C. to a cell density of 4.0 g/L. The cells were harvested and resuspended in Tris-HCl buffer (pH=8.0) to a concentration of 12.3 g/L. After passage through a French press, the cell debris was removed by centrifugation at 45,000 g for 45 min. To this crude cell extract without membrane proteins was added NADH (5 mM). N-benzylpyrrolidine, N-benzyloxycarbonyl-pyrrolidine, and N-tert-butoxycarbonyl-pyrrolidine was added to a final concentration of 5 mM, respectively. The mixture was shaken at 30° C. for 2 h. Analytical and isolation procedures were as described before. The results are listed in table 11.

TABLE 11

Preparation of optically active N-benzyl-3-hydroxy-pyrrolidine, N-benzyloxycarbonyl-3-hydroxypyrrolidine, and N-tert-butoxycarbonyl-3-hydroxy-pyrrolidine with cell extracts (CE) of HXN-200

| Substrate (mM) | Cells for CE[1] (g/L) | NADH (mM) | Yield (%) 15' | 0.5 h | 1 h | 2 h |
|---|---|---|---|---|---|---|
| A: 5 | 12.3 | 5 | 5 | 10 | 14 | 17 |
| B: 5 | 12.3 | 5 | 5 | 6 | 7 | 7 |
| C: 5 | 12.3 | 5 | 11 | 16 | 26 | 26 |

[1]CE derived from a cell suspension of the indicated concentration;
A: N-benzylpyrrolidine;
B: N-benzyloxy-carbonyl-pyrrolidine;
C: N-tert-butoxycarbonyl-pyrrolidine.

Example 17

Preparation of N-acetyl-3-hydroxypyrrolidine in vivo with Resting Cells of Cyclohexane-degrading Strain An cyclohexane degrading strain (isolated with cyclohexane as carbon source by Li, Z. et al, ETH Zurich; in the strain collection of Institute of Biotechnology, ETH Zurich) was inoculated in ¼ of Evans medium without carbon saurce and grown on cyclohexane vapor diluted 10 times by air as carbon source at room temperature for 3 days. The cells were harvested and resuspened to 5 g/L in 50 mM K-phosphate buffer (pH 7.0) N-acetylpyrrolidine was added to a concentration of 2 mM, and the mixture was shaken at 30° C. for 1 day. For following the reaction, samples were taken from the reaction mixture at different time, the cells were removed by centrifugation, and the supernatants were analysed by analytical HPLC [column: Spherisorb ODS2 (5 μm), 125 mm×4 mm; eluent: aceronitrile/10 mM K-phosphate buffer (pH 7.0) 5/95; flow rate: 1 ml/min; detection wavelength; 210 nm; retention time of N-acetyl-3-hydroxypyrrolidine: 2.3 min; retention time of N-acetylpyrrolidine: 7.9 min]. 4% of product was obtained after 1.5 h. The product was identified as N-acetyl-3-hydroxy-pyrrolidine by comparing the GC-MS spectra and NMR spectra with those of the authentic compound.

The invention claimed is:

1. A process for the preparation (If optically active 3-hydroxypyrrolidine or N-substituted 3-hydroxypyrrolidine comprising
    inserting an oxygen atom stereoselectively in to the corresponding non-hydroxylated pyrrolidine compound by using a bacterium having hydroxylation activity as a biocatalyst, wherein said bacterium is an alkane-degrading bacterium or a mono-alicyclic compound-degrading bacterium; and
    separating said optically active 3-hydroxypyrrolidine or N-substituted 3-hydroxypyrrolidine from said corresponding non-hydroxylated pyrrolidine compound.

2. The process of claim 1, wherein said bacterium is a bacterium that degrades an n-alkane containing 4 to 20 carbon atoms.

3. The process of claim 1, wherein said bacterium is a bacterium that degrades n-octane.

4. The process of claim 1, wherein said bacterium is a bacterium that degrades n-hexane.

5. The process of claim 1, wherein said bacterium is a bacterium that degrades monoalicyclic compounds containing 4 to 20 carbon atoms.

6. The process of claim 1, wherein said bacterium is a *Pseudomonas oleovorans* strain.

7. The process of claim 6, wherein the *Pseudomonas oleovorans* strain is *Pseudomonas oleovorans* Gpo1.

8. The process of claim 1, wherein said bacterium is a resting bacterial cell, a growing bacterial cell, or both.

9. The process of claim 1, wherein said bacterium is immobilized on or in a water insoluble carrier or support system.

10. The process of claim 1, wherein the process is performed in aqueous medium.

11. The process of claim 1, wherein the process is performed in multiphase media containing two or more of the following: a solid phase, an aqueous phase, an organic phase, and a gaseous phase.

12. The process of claim 11, wherein said organic phase comprises an organic compound selected from the group consisting of alkanes with at least five carbon atoms, dialkyl ethers with at least four carbon atoms, aromatic hydrocarbons, and heteroaromatic hydrocarbons.

13. The process of claim 1, wherein the process is performed at a reaction temperature of between about 5° to about 50° C.

14. The process of claim 13, wherein the reaction temperature is between about 20° to about 40° C.

15. The process of claim 1, wherein the process is performed at a pH of 4–10.

16. The process of claim 15, wherein the pH of the medium is 6–8.

17. The process of claim 1, wherein the optically active 3-hydroxypyrrolidine or N-substituted 3-hydroxypyrrolidine is separated by column chromatography with an inorganic or organic adsorbent used as a support.

18. The process of claim 1, wherein the optically active 3-hydroxypyrrolidine or N-substituted 3-hydroxypyrrolidine is separated from a reaction mixture by means of extraction, wherein the corresponding non-hydroxylated pyrrolidine compound is first recovered from the reaction mixture by extraction with an apolar solvent, and the optically active 3-hydroxypyrrolidine or N-substituted 3-hydroxypyrrolidine is extracted with a polar solvent.

19. The process of claim 18, wherein an extraction agent selected from the group consisting of alkanes with at least live carbon atoms, dialkyl ethers with at least four carbon atoms, chlorine-containing alkanes with at most three carbon atoms, alkyl aromatics with seven to ten carbon atoms, and carboxylic esters with at least three carbon atoms is used to perform said extraction.

20. The process of claim 1, wherein the optically active 3-hydroxypyrrolidine or N-substituted 3-hydroxypyrrolidine is separated from a reaction mixture by use of membrane filtration.

21. The process of claim 1, wherein the optically active N-substituted 3-hydroxypyrrolidine is N-benzoyl-3-hydroxypyrrolidine.

22. The process of claim 1, wherein the optically active N-substituted 3-hydroxypyrrolidine is N-benzyloxycarbonyl-3-hydroxypyrrolidine.

23. The process of claim 1, wherein the optically active N-substituted 3-hydroxypyrrolidine is N-phenoxycarbonyl-3-hydroxypyrrolidine.

24. The process of claim 1, wherein the optically active N-substituted 3-hydroxypyrrolidine is N-tert-butoxycarbonyl-3-hydroxypyrrolidine.

25. The process of claim 1, wherein the optically active N-substituted 3-hydroxypyrrolidine is N-benzyl-3-hydroxypyrrolidine.

26. The process of claim 1, wherein the bacterium is a *Pseudomonas putida* strain.

27. The process of claim 1, wherein the bacterium is selected from the group of genera consisting of *Pseudomonas, Mycobacterium, Corynebacterium, Nocardia* and *Sphingomonas*.

* * * * *

UNITED STATES PATENT AND TRADEMARK OFFICE
CERTIFICATE OF CORRECTION

PATENT NO.         : 7,141,412 B2                                              Page 1 of 1
APPLICATION NO. : 10/372483
DATED                : November 28, 2006
INVENTOR(S)       : Li et al.

It is certified that error appears in the above-identified patent and that said Letters Patent is hereby corrected as shown below:

Column 22, Line 17, Claim 19       Now reads:       "live carbon atoms"

Should read:    --five carbon atoms--

Signed and Sealed this

Tenth Day of April, 2007

JON W. DUDAS
*Director of the United States Patent and Trademark Office*